(12) United States Patent
Breidenthal et al.

(10) Patent No.: US 10,162,146 B2
(45) Date of Patent: Dec. 25, 2018

(54) OPTO-MECHANICAL APPARATUS ADAPTED FOR MOUNTING OPTICAL ELEMENTS WITH SMALL CROSS SECTIONS

(71) Applicant: Intuitive Surgical Operations, Inc., Sunnyvale, CA (US)

(72) Inventors: Robert S Breidenthal, Bolton, MA (US); Richard Cyr, New Ipswich, NH (US); David Chambers, Warren, MA (US); Joseph N Forkey, Princeton, MA (US); Robert N Ross, Gardner, MA (US); Brian E Volk, Jefferson, MA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 31 days.

(21) Appl. No.: 13/892,953

(22) Filed: May 13, 2013

(65) Prior Publication Data
US 2013/0301148 A1    Nov. 14, 2013

Related U.S. Application Data

(60) Provisional application No. 61/646,760, filed on May 14, 2012.

(51) Int. Cl.
*G02B 7/02* (2006.01)
*G02B 23/24* (2006.01)
*A61B 1/00* (2006.01)

(52) U.S. Cl.
CPC .............. *G02B 7/02* (2013.01); *A61B 1/0011* (2013.01); *A61B 1/00096* (2013.01); *G02B 7/025* (2013.01); *G02B 23/2476* (2013.01)

(58) Field of Classification Search
CPC .......... G03B 3/10; G03B 17/14; G03B 13/36; G03B 2205/0046; G03B 17/00;
(Continued)

(56) References Cited

U.S. PATENT DOCUMENTS

2001/0033436 A1* 10/2001 Hunter ................... G02B 7/026
                                                    359/819
2002/0161278 A1* 10/2002 Nakamura ......... A61B 1/00096
                                                    600/111
(Continued)

FOREIGN PATENT DOCUMENTS

| JP | 2011145505 A | | 7/2011 | |
| JP | O 2011-145505 | * | 7/2011 | ............... G02B 7/02 |
| SU | 1697038 A1 | | 7/1991 | |

OTHER PUBLICATIONS

JPO 2011-145505 English Machine Translation.*
(Continued)

*Primary Examiner* — Thomas K Pham
*Assistant Examiner* — Sharrief Broome (57) ABSTRACT

An opto-mechanical assembly including a housing and an internally supported optical element, such as a lens, mounted along an axis. At least one of the housing and optical element includes a radially extending chamber. Adhesive disposed in the chamber interacts with the housing and the optical element to prevent axial motion between the optical element and housing.

20 Claims, 7 Drawing Sheets

(58) Field of Classification Search
CPC ............... G03B 17/12; G03B 17/565; G03B 2205/0061; G03B 2205/0084; G03B 5/00; G03B 11/00; G03B 13/00; G03B 13/32; G03B 17/08; G03B 17/563; G03B 17/566; G03B 19/00; G03B 17/17; G02B 7/04; G02B 7/08; G02B 7/023; G02B 7/09; G02B 7/10; G02B 7/02; G02B 7/026; G02B 13/001; G02B 7/021; G02B 7/022; G02B 7/028; G02B 7/102; G02B 7/14; G02B 13/009; G02B 27/646; G02B 7/003; G02B 7/025; G02B 25/002; G02B 2207/125; H04N 5/2259; H04N 13/0282; H04N 5/2254; H01L 27/1462; H01L 27/14623; H01L 27/14625; H01L 27/14627; H01L 27/14629; H01L 27/14818; G06K 9/209; G08B 13/19626; G08B 13/19628
USPC .................... 359/694, 700, 811–824, 826
See application file for complete search history.

(56) References Cited

U.S. PATENT DOCUMENTS

| | | | | |
|---|---|---|---|---|
| 2008/0007848 A1* | 1/2008 | Minami | ............... | G02B 7/021 359/819 |
| 2011/0075278 A1* | 3/2011 | Nagaoka et al. | ............. | 359/819 |
| 2013/0063655 A1* | 3/2013 | Hsu | ............... | G02B 7/021 348/374 |
| 2014/0204476 A1* | 7/2014 | Takase | ............... | G02B 7/021 359/738 |

OTHER PUBLICATIONS

International Search Report PCT/US2013/050443 dated Nov. 7, 2013.

Spravochnik konstruktora optiko-mekhanicheskikh priborov pod red. V.A. Panaova. Leningrad, "Mashinostroenic", Leningradskoe otdelenie, 1980, p. 276-277.

* cited by examiner

OPTO-MECHANICAL APPARATUS ADAPTED FOR MOUNTING OPTICAL ELEMENTS WITH SMALL CROSS SECTIONS

CROSS REFERENCE TO RELATED APPLICATION

This application claims priority from U.S. Provisional Patent Application No. 61/646,760 for Opto-Mechanical Apparatus Adapted for Mounting Optical Elements with Small Cross Sections filed May 14, 2012 and assigned to the application of this invention

BACKGROUND OF THE INVENTION

Field of the Invention

This invention generally relates to optical-mechanical apparatus and more specifically to opto-mechanical apparatus having a small cross section that includes a housing and an optical element.

Description of Related Art

A significant effort has been made and continues to be made toward the development of opto-mechanical apparatus with increasingly smaller transverse cross sections. This is particularly true in the medical field where diagnosis and related treatment regimens for endoscopic devices is expanding with the introduction of smaller, reliable and reasonably priced opto-mechanical apparatus. Presently there are efforts underway to produce cylindrical lenses that have diameters less than 2 mm and even in the range of 1 mm or less.

Such small opto-mechanical apparatus generally has several major components. For purposes of describing this invention there are two such components, namely: (1) an optical element that may comprise a lens, an optical window or combination of one or more of each and (2) a housing that supports each optical element on an optical axis. As the demand for smaller and smaller diameter lenses continues to increase, new problems have emerged that can detract from the efficacy of such new apparatus. First, the housing can overlie the imaging surface of an optical element and thereby reduce the optical field of view for that apparatus. Second, the method by which the optical device is retained in the housing can fail during use. Third, such apparatus must be constructed so that its exterior surface is smooth for easy cleaning.

Figure 1:
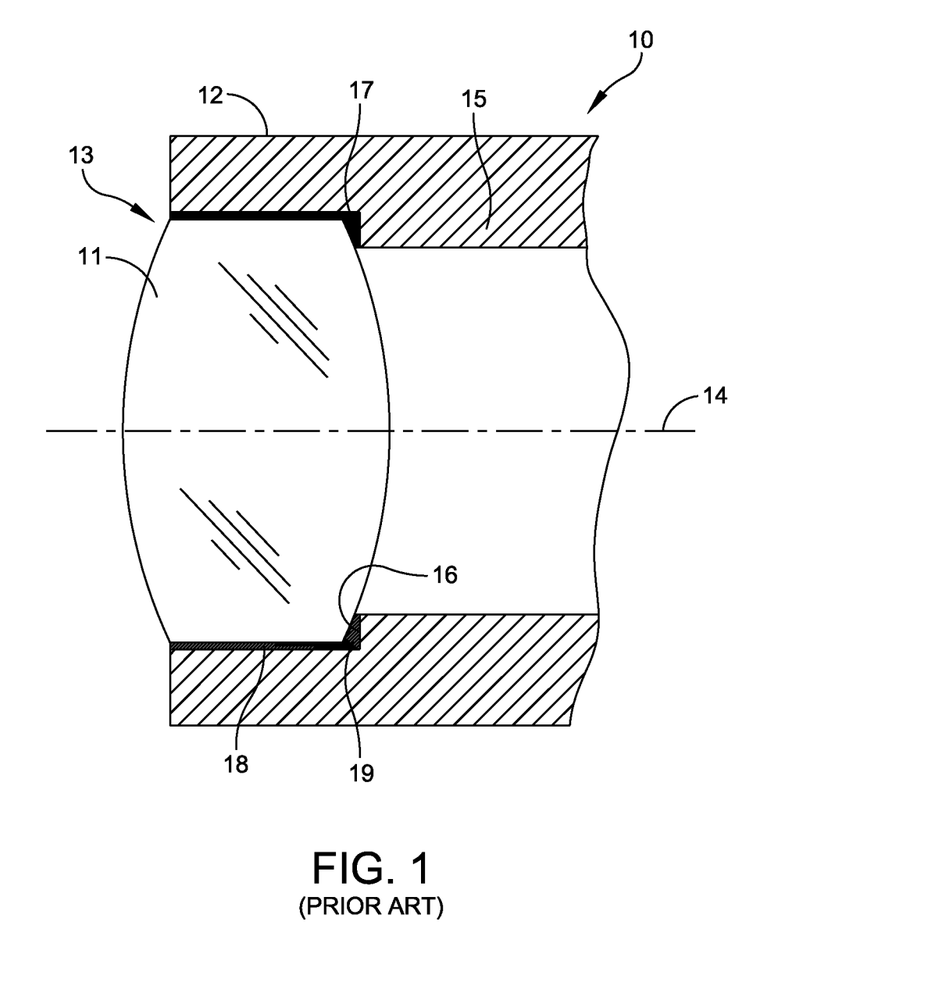
FIG. 1 is a cross section of one embodiment of a conventional prior art opto-mechanical assembly in which an adhesive locks an optical element constituted by a lens in a housing.

FIG. 1 depicts a prior art opto-mechanical assembly 10 that maximizes the field of view, but includes a retaining structure that is subject to failure. The assembly 10 includes a conventional biconvex lens 11 as an optical element. A housing 12 has a distal end 13 and aligns the lens 11 along an optical axis 14. The right side of the assembly 10 in FIG. 1 extends to a proximal end (not shown, but known in the art). The housing 12 also contains an integral, radially inwardly extending band 15 that forms a shoulder or seat 16 against which the proximal side of the lens 11 seats. Adhesive material 17 fills gaps 18 and 19 between the outer periphery of the lens 11 and the coextensive spaced inner surfaces of the housing 12. When completed, the distal ends of the lens 11 and the housing 12 are flush and create a smooth surface to facilitate cleaning and reduce contamination during use by eliminating any crevices or the like in the apparatus. The retention of the lens 11 within the housing 12 of this apparatus 10, however, depends solely upon the adhesion that exists between the adhesive material 17 and the adjacent surfaces of the lens 11 and housing 12. Such adhesion, in turn, depends upon the contact area for the adhesive material that, in the configuration of FIG. 1, is proportional to lens diameter and length. Adhesion is also dependent upon the surface roughness and the materials that contact the adhesive material.

Such opto-mechanical assemblies can be subjected to environmental conditions that create forces on the bonds produced by the adhesive material. Such forces can be generated by accident, as by exposing the bond to a mechanical shock, by dropping the assembly, or by wide temperature or other environmental factors that produce differential expansions of the lens 11 and the housing 15. If such a force is large enough to exceed the adhesion characteristics of the adhesive material 17, the adhesive material could decouple from the lens 11 and/or housing 12 whereupon the bi-convex lens 11 could shift distally and become unstable axially or even completely separate from the housing 12. In either event, the opto-mechanical assembly 10 would require factory repair or even replacement. Also, if the lens 11 were to separate from the housing 12, negative consequences for the procedure being performed with the assembly could result. Thus, as will be apparent to those skilled in the art, the specific opto-mechanical assembly in FIG. 1 provides a maximum field of view and smooth distal surface, but a less than optimal resistance to shock and other environmental factors.

Figure 2A:
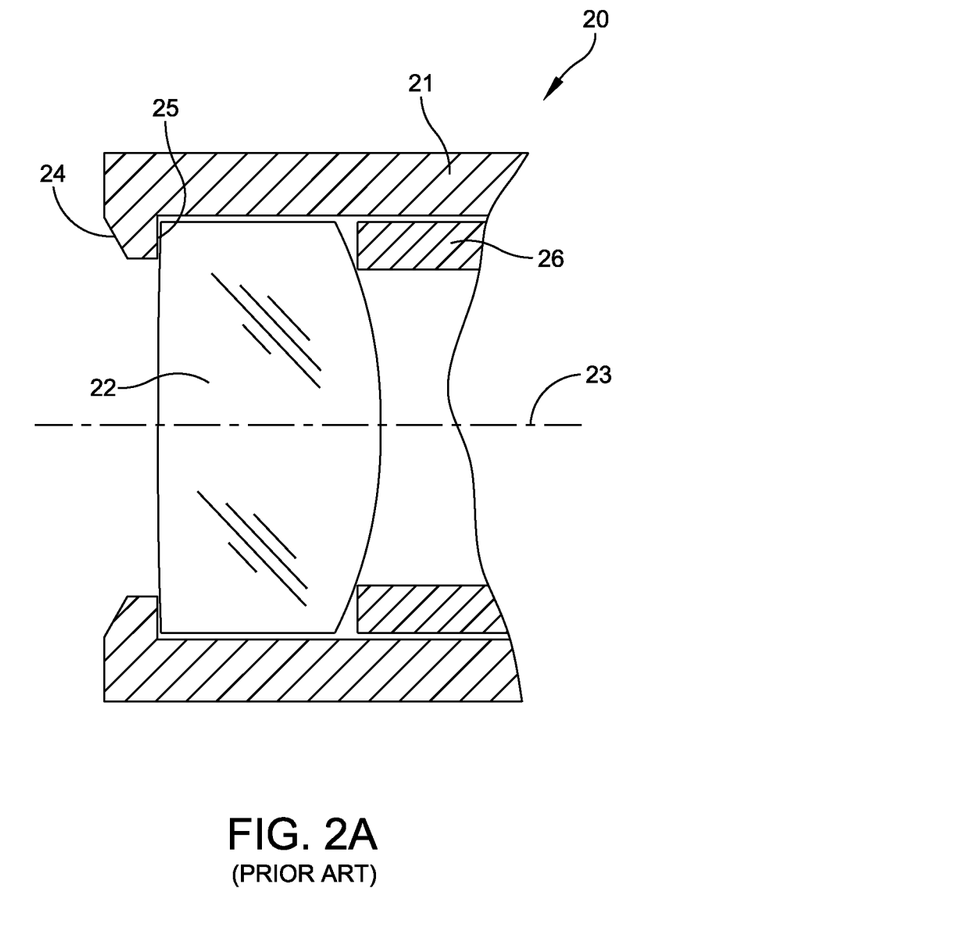
FIGS. 2A and 2B are cross sections of embodiments of a conventional prior art opto-mechanical assemblies in which an optical element constituted by a lens is locked within a housing by mechanical means.
Figure 2B:
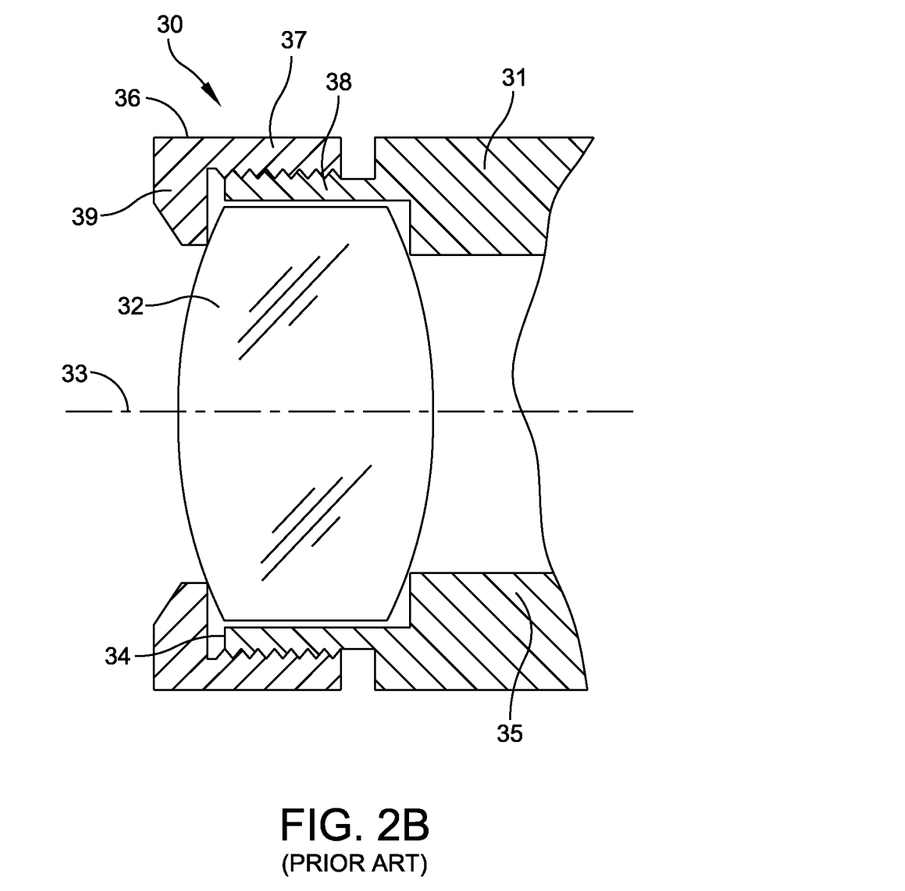

FIGS. 2A and 2B depict variations of opto-mechanical assemblies that utilize mechanical retention structures that, as will become apparent, strengthen the retention characteristics, but also decrease field of view and result in non-smooth surfaces. FIG. 2A discloses an opto-mechanical assembly 20 with a housing 21 and a plano-convex lens 22. The opto-mechanical assembly 20 has an optical axis 23. In this variation, an angular radially inwardly extending lip 24 forms a positioning stop 25 that blocks any distal shift of the lens 22. During manufacture, the lens 22 is inserted from the proximal end of housing 21 until it reaches the shoulder 25. Thereafter, a mechanical element such as a lens spacer 26 is inserted into the housing 21 from the proximal end. Other means lock the lens spacer 26 into its axial position so the lens spacer 26 blocks any proximal shift of the lens 22.

In the other variation of FIG. 2B an opto-mechanical assembly 30 includes a housing 31 with a bi-convex lens 32 extending along an optical axis 33. The lens 32 is loaded into the housing from the distal end 34 until it contacts a shoulder on a positioning band 35 that is integral with the housing 31 thereby to block any further proximal lens shift. At a distal end 34, the housing 31 receives a retainer element 36 that includes an internally threaded extension 37 that mates with an axially distally extending extension 38 from the housing 31. A radially inwardly extending lip 39 engages the lens 32 and prevents any distal lens shift of the lens 32.

Each of these embodiments provides a structure that blocks any proximal or distal shift and that can withstand mechanical shock, and other environmental conditions that generate forces between the optical and mechanical elements. However, the lip 24 in FIG. 2A and the lip 39 in FIG. 2B limit the field of view because they overlap the distal ends of the lenses 22 and 32 respectively, thereby reducing their clear apertures and because they extend axially beyond the distal lens surface. In addition, as these retaining structures extend beyond the distal surface of their respective lenses, the distal surface of the lens 22 in FIG. 2A and the distal surface of the lens 32 in FIG. 2B are not flush with the distal most surfaces of the housings 21 and 32, respectively. Cleaning of the exterior surface, which is not smooth, is therefore more difficult due to the interior angles. These non-smooth surfaces also act as locations for buildup of contamination during use. For an opto-mechanical assembly of a given size, the cost of adding in separate locking elements and fastening them in a secure manner increases the expense of manufacture. Moreover, as the apparatus size decreases, manufacturing complexity and concomitant costs increase. In fact for lens assemblies that are very small, for example less than 2 mm, the cost of adopting such a construction technique can become commercially and technically prohibitive.

What is needed is an opto-mechanical assembly that is adapted for including small optical elements in a small housing that optimizes field of view, that optimizes the mechanical structure for reliable mechanical containment and that facilitates cleaning. What also is needed is such an apparatus that is commercially and technically feasible.

SUMMARY OF THE INVENTION

Therefore it is an object of this invention to provide an opto-mechanical assembly that provides a reliable mechanical connection between an optical element and a housing for carrying that optical element.

Another object of this invention is to provide an opto-mechanical assembly in which one surface of an optical element is flush with one end of a housing and in which any axial shift of the optical element is blocked.

Still another object of this invention is to provide an opto-mechanical assembly that provides a reliable mechanical connection for an optical supporting housing and that maximizes field of view.

Yet another object of this invention is to provide an opto-mechanical assembly that provides a reliable mechanical connection for an optical element in a supporting housing and that is commercially and technologically feasible.

In accordance with one aspect of this invention, an opto-mechanical assembly as at last one end and comprises an optical element, a mechanical housing, a cavity in at least one of said optical element and mechanical housing, and adhesive in each cavity. The optical element has first and second polished end surfaces and an intermediate body portion through which light passes and has a given outer periphery and a given cross section transverse to an optical axis for the opto-mechanical assembly. The mechanical housing positions the optical element along the optical axis at the one end so that the first polished end surface of the optical element is substantially flush with the one end of the mechanical housing. A cavity is formed in one of the optical element and mechanical housing. The mechanical properties of the adhesive in the cavity enable the adhesive to lock the optical element axially within the mechanical housing independently of any adhesive bond.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 3:
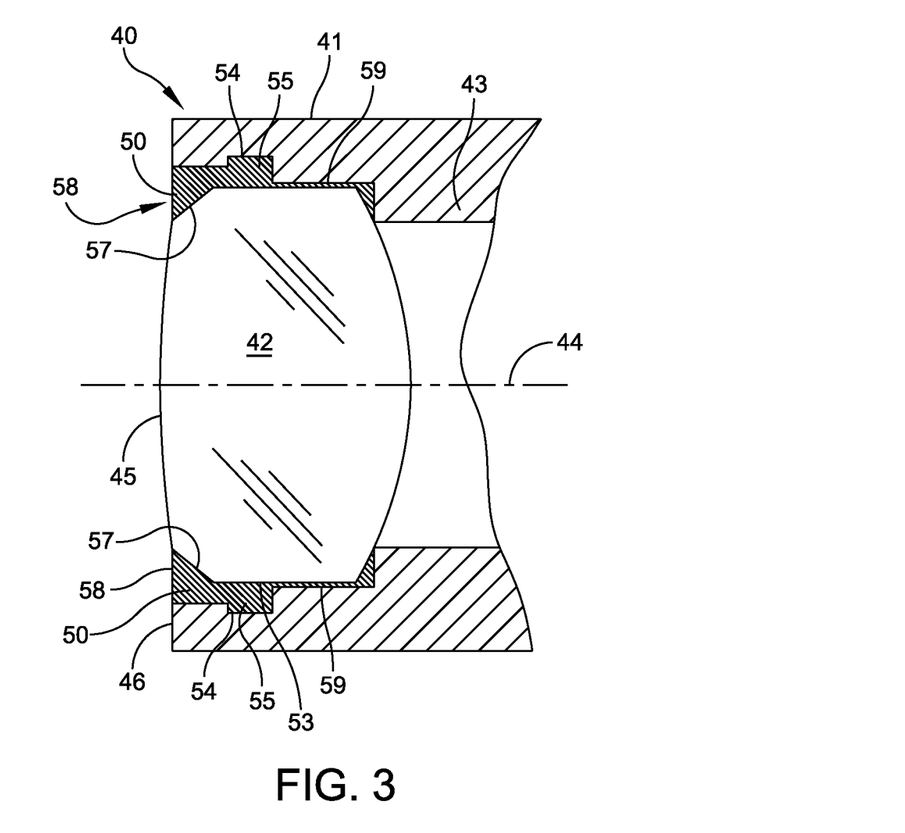
FIG. 3 is a cross section of one embodiment of an opto-mechanical assembly that embodies this invention.

In FIG. 3 an opto-mechanical assembly 40 includes a mechanical housing 41 and an optical element in the form of a bi-convex lens 42. As known, such lenses have first and second end surfaces and an intermediate body portion through which light passes. A specific optical element may have a circular or polygonal cross section and other peripheral features. In FIG. 3 the bi-convex lens is cylindrical.

The mechanical housing 41 includes an integral positioning band 43 that forms an annular stop for blocking any proximal shift of the lens 42 (i.e., to the right in FIG. 3). The housing 41 also supports the lens 42 along an optical axis 44. The positioning band 43 locates the lens 42 so its distal surface 45 is flush with a distal end surface 46 of the housing 41.

In accordance with this invention, adhesive 50 is disposed about the periphery of the lens 42 and the corresponding surfaces of the housing 41. More specifically and referring to FIGS. 3 and 4, the housing 41 includes a lens body engaging portion 51 with a diameter that is slightly larger than the lens diameter such that a gap exists between the surfaces 52 of the housing 41 and 53 of the lens 42. A peripherally extending annular channel 54 forms an inwardly facing cavity 55 that is intermediate the housing distal end surface 46 and is distal to the positioning band 43. The housing also defines a reduced diameter opening 56 that extends from the channel 54 to the distal end surface 46.

Still referring to FIG. 3, the distal surface 45 of the lens 42 is beveled at 57 to form a relief that defines a second cavity 58 between the inner surface of the housing 41 and channel 54. The cavities 55 and 58 have openings facing each other. Thus when adhesive material 50 fills the cavities 55 and 58 and a peripheral gap 59, the adhesive material 50 in the first and second cavities 55 and 58 maximizes the retentive function of the adhesive material and minimizes its failure due to shock. This occurs because failure of the adhesive material structure requires a greater force than is necessary to overcome the bonding forces in the apparatus of FIG. 1 for smaller lenses. As will also be apparent, the addition of the elements in the apparatus of FIG. 3 reduces the field of view of the optical element, such as the lens 42, less than would a mechanical retainer extending distally to the surface of the lens 42.

Figure 5:
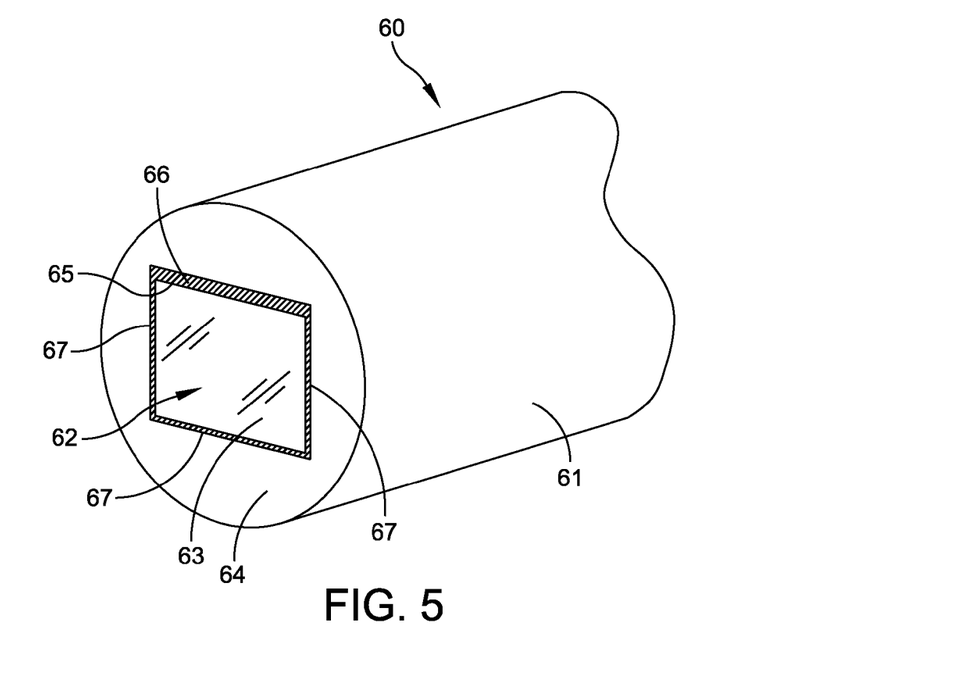
FIG. 5 is a perspective view of another embodiment of an opto-mechanical assembly that incorporates this invention.
Figure 6:
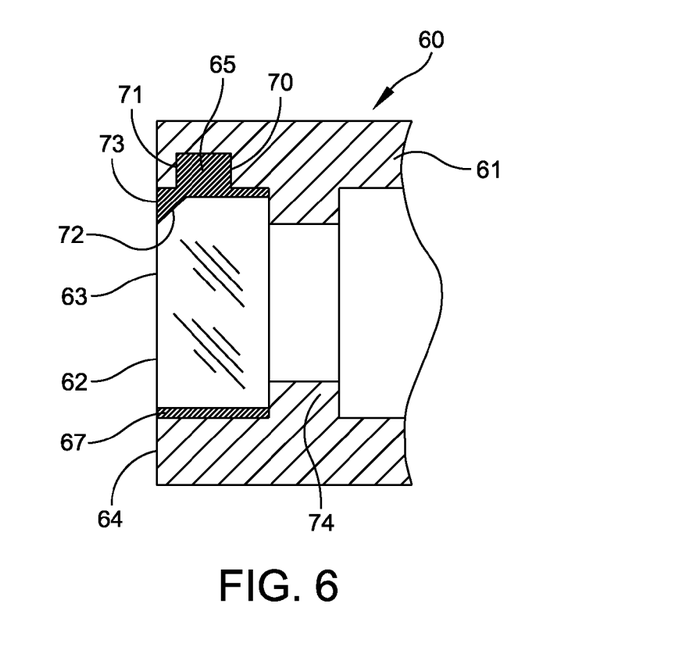
FIG. 6 is a cross section of a portion of the opto-mechanical assembly shown in FIG. 5

FIGS. 1, 2A, 2B and 3 disclose cross sections of circular housings and cylindrical lenses. FIGS. 5 and 6 depict a view of the distal end of a completed opto-mechanical assembly 60 with a cylindrical housing 61 that supports a rectangular optical window 62 in a matching rectangular passage such that the distal surface 63 of the optical window 62 is flush with the distal end surface 64 of the housing 61. Adhesive material 65 appears as a wide band 66 across one side of the optical window 62 and as narrow bands 67 along the other sides of the optical window 62. Other patterns of adhesive placement could be substituted for the specifically disclosed pattern.

As shown in more detail in FIG. 6, the housing includes a relief in the form of a channel 70 formed in one side of the housing passage surface that defines a housing cavity 71 that opens toward a coextensive portion of the optical window 62. The optical window 62 has a relief in the form of a bevel 72 that defines a second cavity 73 that opens toward the first cavity 71. The openings of the cavities 71 and 73 in FIG. 6 also enable the adhesive material 65 to fill each of the cavities 71 and 73. The adhesive material 65 between the edge of the optical window 62 and the coextensive surfaces of the housing passage forms a continuous adhesive body with portions in each of the cavities 71 and 73. The housing is also formed with an internal positioning band 74 for seating the optical window 62 and blocking any proximal shift of the optical window 62 after assembly. Similarly to FIG. 3, the opto-mechanical assembly 60 of FIG. 6 includes adhesive material 65 in the cavities 71 and 73 to form a mechanical structure that blocks any distal shift of the optical window 62, even in the event of failure of the adhesive properties of the adhesive material. As will also be apparent, the addition of the cavities 71 and 73 and contained adhesive material 65 does not reduce the field of view for the opto-mechanical apparatus 60 as much as would a mechanical retainer extending distally to the surface of the window 62.

Figure 7:
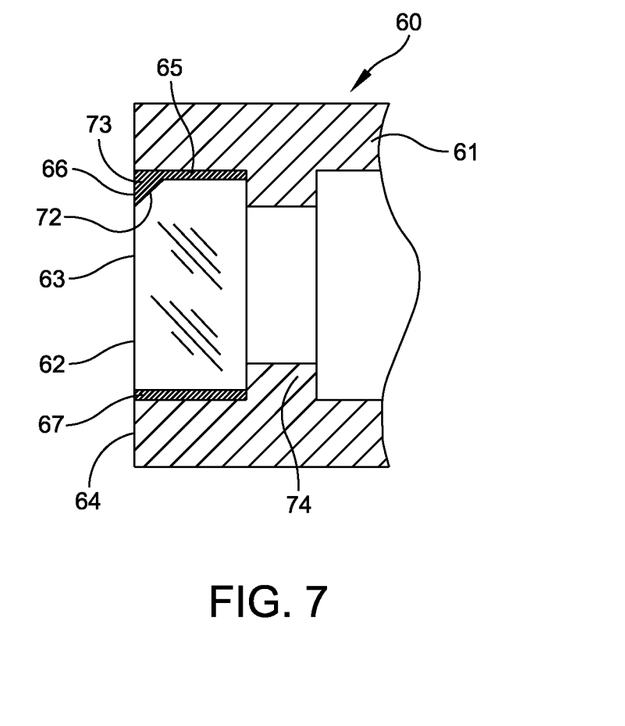
FIG. 7 depicts an alternate embodiment of the opto-mechanical assembly shown in FIG. 6.

FIG. 7 depicts another version of opto-mechanical assembly 60 of FIG. 6. This embodiment is useful when there is only a minimal risk of failure of one of the adhesive bonds, particularly the bond between the adhesive material 65 and the housing 61 during specified use of the opto-mechanical assembly 60. Using the reference numbers of FIG. 6, this variation of the opto-mechanical assembly 60 in FIG. 7 has the cylindrical housing 61 that supports the rectangular optical window 62 such that the distal surface 63 of the optical window 62 is flush with the distal end surface 64 of the housing 61. Adhesive material 65 appears as a wide band 66 across one side of the optical window 62 and as narrow bands 67 along the other sides of the optical window 62. If the bond between the adhesive 65 and the lens 63 were to fail without breakage of the adhesive, the adhesive in the wide band 66 mechanically locks the lens 63 axially in place independently of any bond failure. That is, in FIG. 7, the cavity 70 shown in FIG. 6 is eliminated.

As will now be apparent, the embodiments of this invention shown in FIG. 3 connection between an optical element and a supporting housing. Each provides an apparatus in which an exterior surface of an optical element is flush with a corresponding housing surface for easy cleaning. Each provides an optical apparatus in which the disclosed retention structure minimizes the reduction of the field of view for the apparatus and that is commercially and technologically feasible to manufacture.

Figure 4:
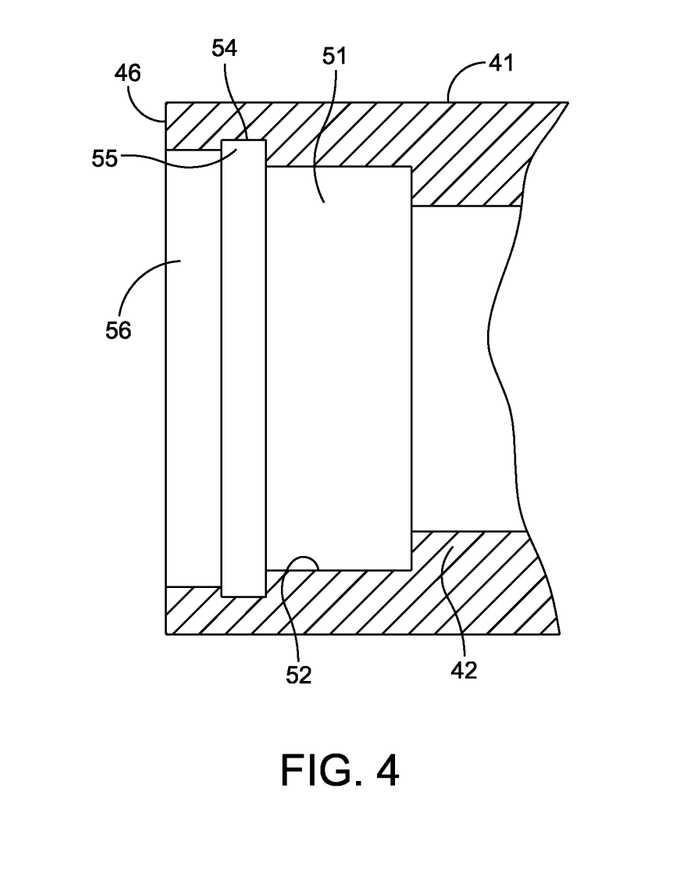
FIG. 4 is a cross section of a housing used in the opto-mechanical assembly embodiment of FIG. 3.

This invention has been disclosed in terms of certain embodiments. It will be apparent that many modifications can be made to the disclosed apparatus without departing from the invention. For example, the disclosed optical apparatus includes lenses of different shapes. For different implementations apparatus incorporating this invention could include lenses of other shapes or types. FIGS. 3 and 4 disclose cavities that extend about the cylindrical inner surface of a housing. FIGS. 5 through 7 disclose rectangular optical elements with cavities positioned only along one complete side. In other embodiments a cavity may extend only over a portion of a specific surface. Specifically disclosed cavity cross-sections may be replaced by cavities of different cross-sections. Each of the embodiments in FIGS. 3, 5 and 7 depict apparatus wherein the adhesive is applied axially from the distal end of the apparatus. As an alternative more radial fill holes could be incorporated in a housing for directing adhesive from a supply through the wall of the housing to a channel or other gap between the housing and the lens. Therefore, it is the intent of the appended claims to cover all such variations and modifications as come within the true spirit and scope of this invention.

What is claimed as new and desired to be secured by Letters Patent of the United States is:

1. An opto-mechanical assembly comprising:
    an optical lens having first and second polished end surfaces with the first polished end surface including a first beveled portion, an intermediate body portion through which light passes, and a cross-section transverse to an optical axis of the opto-mechanical assembly;
    a mechanical housing configured to position said optical lens along the optical axis at a distal end so that said first polished end surface, that includes said first beveled portion, is substantially flush with said distal end of said mechanical housing; and
    a first cavity formed between a first inner surface of said mechanical housing and said first beveled portion, wherein
    said first beveled portion is enclosed within said mechanical housing, and
    an adhesive is positioned in said first cavity, wherein a positioning of the adhesive within the first cavity mechanically locks the optical lens axially within said mechanical housing independently of any adhesive bond between the adhesive and the optical lens to thereby prevent a distal shift of the optical lens.

2. The opto-mechanical assembly of claim 1, further including a plurality of cavities formed between said first inner surface of a portion of said mechanical housing and said optical lens.

3. The opto-mechanical assembly of claim 1, wherein
    said cross-section of said optical lens is a cylindrical cross section; and
    said first cavity extends radially to comprise at least a portion of said cross-section of said optical lens.

4. The opto-mechanical assembly of claim 1, wherein said first cavity comprises a circumferential channel formed of said first inner surface of said mechanical housing intermediate said first beveled portion and a proximal end of said mechanical housing.

5. The opto-mechanical assembly of claim 1, wherein a peripheral gap exists between an outer peripheral surface of said optical lens and the first inner surface of said mechanical housing, said adhesive filling at least a portion of said peripheral gap.

6. The opto-mechanical assembly of claim 1, wherein said cross-section of said optical lens is a rectangular transverse cross section.

7. The opto-mechanical assembly of claim 6, wherein said first cavity in said mechanical housing is proximate one side of said optical lens.

8. The opto-mechanical assembly of claim 7, wherein the adhesive fills at least a portion of a gap between the mechanical housing and sides of said optical lens.

9. The opto-mechanical assembly of claim 1, wherein said first polished end of said optical lens includes a second beveled portion to form a second cavity between a second inner surface of said mechanical housing and said second beveled portion.

10. The opto-mechanical assembly of claim 9, wherein said second cavity in said mechanical housing forms an inwardly opening channel facing said optical lens element whereby adhesive fills said inwardly opening channel.

11. An opto-mechanical assembly, comprising:
an optical lens having a polished end surface with a beveled portion;
a housing configured to position the optical lens at a distal end and along an optical axis of the opto-mechanical assembly, an inner surface of the housing having a recessed portion;
a first cavity between the optical lens and the recessed portion;
a second cavity between the beveled portion of the optical lens and the inner surface of the housing; and
an adhesive positioned within the first cavity and the second cavity, wherein a positioning of the adhesive within the first cavity and the second cavity mechanically locks the optical lens axially within the housing independently of a first adhesive bond between the adhesive and the optical lens and independently of a second adhesive bond between the adhesive and the inner surface of the housing to thereby prevent a distal shift of the optical lens.

12. The opto-mechanical assembly of claim 11, wherein the polished end surface is substantially flush with the distal end of the housing.

13. The opto-mechanical assembly of claim 12, wherein a surface of the adhesive at the distal end of housing is substantially flush with the distal end of the housing.

14. The opto-mechanical assembly of claim 11, wherein the housing has a lens engaging portion.

15. The opto-mechanical assembly of claim 11, wherein the optical lens has a cross-section that is transverse to the optical axis of the opto-mechanical assembly.

16. The opto-mechanical assembly of claim 11, wherein the adhesive fills a peripheral gap formed between a lens engaging portion of the housing and the optical lens.

17. The opto-mechanical assembly of claim 1, wherein the optical axis passes through the first and second polished end surfaces, and the optical lens has third and fourth end surfaces parallel to the optical axis, the adhesive contacting the third and fourth end surfaces.

18. The opto-mechanical assembly of claim 10, wherein a positioning of the adhesive in the second cavity forms a mechanical structure that blocks the distal shift of the optical lens independently of any adhesive bond between the adhesive and the housing.

19. The opto-mechanical assembly of claim 1, wherein the distal end of the mechanical housing, a surface of the adhesive in the first cavity, and at least a portion of the first polished end surface are substantially flush with each other and form a continuous surface that is substantially planar.

20. The opto-mechanical assembly of claim 11, wherein the polished end surface is transverse to the optical axis.

* * * * *